US008660638B2

(12) United States Patent
Stahmann et al.

(10) Patent No.: US 8,660,638 B2
(45) Date of Patent: Feb. 25, 2014

(54) SYNCOPE LOGBOOK AND METHOD OF USING SAME

(75) Inventors: Jeffrey E. Stahmann, Ramsey, MN (US); John D. Hatlestad, Maplewood, MN (US); Jesse W. Hartley, White Bear Lake, MN (US); Avram Scheiner, Vadnais Heights, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1141 days.

(21) Appl. No.: 12/616,536

(22) Filed: Nov. 11, 2009

(65) Prior Publication Data

US 2010/0056929 A1 Mar. 4, 2010

Related U.S. Application Data

(63) Continuation of application No. 11/121,450, filed on May 4, 2005, now Pat. No. 7,630,755.

(51) Int. Cl.
*A61B 5/0402* (2006.01)
(52) U.S. Cl.
USPC ........................................................ 600/509
(58) Field of Classification Search
None
See application file for complete search history.

(56) References Cited

U.S. PATENT DOCUMENTS

| | | | |
|---|---|---|---|
| 4,519,395 A | 5/1985 | Hrushesky | |
| 4,562,841 A | 1/1986 | Brockway et al. | |
| 4,702,253 A | 10/1987 | Nappholz et al. | |
| 4,763,663 A | 8/1988 | Uphold et al. | |
| 4,809,697 A | 3/1989 | Causey et al. | |
| 4,813,427 A | 3/1989 | Schlaefke et al. | |
| 4,830,008 A | 5/1989 | Meer | |
| 4,930,517 A | 6/1990 | Cohen et al. | |
| 4,930,518 A | 6/1990 | Hrushesky | |
| 5,036,849 A | 8/1991 | Hauck et al. | |
| 5,123,425 A | 6/1992 | Shannon, Jr. et al. | |
| 5,165,417 A | 11/1992 | Murphy, Jr. et al. | |
| 5,203,348 A | 4/1993 | Dahl et al. | |
| 5,211,173 A | 5/1993 | Kallok et al. | |
| 5,215,082 A | 6/1993 | Kallok et al. | |
| 5,218,969 A | 6/1993 | Bredesen et al. | |
| 5,230,337 A | 7/1993 | Dahl et al. | |
| 5,284,136 A | 2/1994 | Hauck et al. | |
| 5,313,953 A | 5/1994 | Yomtov et al. | |
| 5,342,404 A | 8/1994 | Alt et al. | |
| 5,360,442 A | 11/1994 | Dahl et al. | |

(Continued)

FOREIGN PATENT DOCUMENTS

EP 1172125 1/2002
WO WO9904841 4/1999

OTHER PUBLICATIONS

International Preliminary Examination Report dated Jul. 31, 2006 from PCT Application No. PCT/US03/040968, 5 pages.
File History for U.S. Appl. No. 10/331,175.

(Continued)

*Primary Examiner* — Michael Kahelin
(74) *Attorney, Agent, or Firm* — Brooks, Cameron & Huebsch, PLLC

(57) ABSTRACT

Methods and systems are directed to acquiring and organizing information associated with at least one syncope event. A syncope event may be a suspected syncope event, a verified syncope event or a syncope event that is suspected and verified. Automated processes are used to collect information associated with at least one syncope event and organize the information as a syncope log entry. At least one of acquiring the information and organizing the information is performed at least in part implantably.

20 Claims, 7 Drawing Sheets

(56) References Cited

U.S. PATENT DOCUMENTS

| | | | |
|---|---|---|---|
| 5,366,496 A | 11/1994 | Dahl et al. |
| 5,376,476 A | 12/1994 | Eylon |
| 5,388,578 A | 2/1995 | Yomtov et al. |
| 5,391,200 A | 2/1995 | Kenknight et al. |
| 5,397,342 A | 3/1995 | Heil, Jr. et al. |
| 5,411,031 A | 5/1995 | Yomtov |
| 5,441,525 A | 8/1995 | Shelton et al. |
| 5,447,164 A | 9/1995 | Shaya et al. |
| 5,464,434 A | 11/1995 | Alt |
| 5,466,245 A | 11/1995 | Spinelli et al. |
| 5,472,453 A | 12/1995 | Alt |
| 5,483,969 A | 1/1996 | Testerman et al. |
| 5,487,755 A | 1/1996 | Snell et al. |
| 5,522,862 A | 6/1996 | Testerman et al. |
| 5,540,727 A | 7/1996 | Tockman et al. |
| 5,545,202 A | 8/1996 | Dahl et al. |
| 5,584,868 A | 12/1996 | Salo et al. |
| 5,603,732 A | 2/1997 | Dahl et al. |
| 5,645,570 A | 7/1997 | Corbucci |
| 5,692,497 A | 12/1997 | Schnitzer et al. |
| 5,836,987 A | 11/1998 | Baumann et al. |
| 5,844,680 A | 12/1998 | Sperling |
| 5,888,187 A | 3/1999 | Jaeger et al. |
| 5,891,023 A | 4/1999 | Lynn |
| 5,911,218 A | 6/1999 | DiMarco |
| 5,913,879 A | 6/1999 | Ferek-Petric et al. |
| 5,916,243 A | 6/1999 | KenKnight et al. |
| 5,928,156 A | 7/1999 | Krumbiegel et al. |
| 5,987,352 A | 11/1999 | Klein et al. |
| 6,026,324 A | 2/2000 | Carlson |
| 6,044,297 A | 3/2000 | Sheldon et al. |
| 6,044,298 A | 3/2000 | Salo et al. |
| 6,047,211 A | 4/2000 | Swanson et al. |
| 6,049,735 A | 4/2000 | Hartley et al. |
| 6,055,454 A | 4/2000 | Heemels |
| 6,099,479 A | 8/2000 | Christopherson et al. |
| 6,116,241 A | 9/2000 | Huygen et al. |
| 6,139,505 A | 10/2000 | Murphy |
| 6,141,590 A | 10/2000 | Renirie et al. |
| 6,142,950 A | 11/2000 | Allen et al. |
| 6,168,568 B1 | 1/2001 | Gavriely |
| 6,216,702 B1 | 4/2001 | Gjersoe |
| 6,240,316 B1 | 5/2001 | Richmond et al. |
| 6,259,948 B1 | 7/2001 | Florio et al. |
| 6,263,244 B1 | 7/2001 | Mann et al. |
| 6,264,606 B1 | 7/2001 | Ekwall et al. |
| 6,269,269 B1 | 7/2001 | Ottenhoff et al. |
| 6,270,457 B1 | 8/2001 | Bardy |
| 6,275,727 B1 | 8/2001 | Hopper et al. |
| 6,280,380 B1 | 8/2001 | Bardy |
| 6,312,378 B1 | 11/2001 | Bardy |
| 6,336,903 B1 | 1/2002 | Bardy |
| 6,351,670 B1 | 2/2002 | Kroll |
| 6,390,091 B1 | 5/2002 | Banner et al. |
| 6,397,845 B1 | 6/2002 | Burton |
| 6,398,728 B1 | 6/2002 | Bardy |
| 6,409,675 B1 | 6/2002 | Turcott |
| 6,411,840 B1 | 6/2002 | Bardy |
| 6,415,175 B1 | 7/2002 | Conley et al. |
| 6,415,183 B1 | 7/2002 | Scheiner et al. |
| 6,438,407 B1 | 8/2002 | Ousdigian et al. |
| 6,449,503 B1 | 9/2002 | Hsu |
| 6,449,504 B1 | 9/2002 | Conley et al. |
| 6,456,256 B1 | 9/2002 | Amundson et al. |
| 6,480,733 B1 | 11/2002 | Turcott |
| 6,580,944 B1 | 6/2003 | Katz et al. |
| 6,589,187 B1 | 7/2003 | Dirnberger et al. |
| 6,668,188 B2 | 12/2003 | Sun et al. |
| 6,719,701 B2 | 4/2004 | Lade |
| 6,741,885 B1 | 5/2004 | Park et al. |
| 6,795,732 B2 | 9/2004 | Stadler et al. |
| 6,810,287 B2 | 10/2004 | Zhu et al. |
| 6,820,618 B2 | 11/2004 | Banner et al. |
| 6,843,801 B2 | 1/2005 | Conley et al. |
| 6,881,192 B1 | 4/2005 | Park |
| 6,895,275 B2 | 5/2005 | Markowitz et al. |
| 6,915,157 B2 | 7/2005 | Bennett et al. |
| 6,949,075 B2 | 9/2005 | Hatlestad et al. |
| 6,964,641 B2 | 11/2005 | Cho et al. |
| 6,974,413 B2 | 12/2005 | Bardy |
| 7,025,730 B2 | 4/2006 | Cho et al. |
| 7,089,936 B2 | 8/2006 | Madaus et al. |
| 7,092,757 B2 | 8/2006 | Larson et al. |
| 7,155,275 B2 | 12/2006 | Linder et al. |
| 7,207,945 B2 | 4/2007 | Bardy |
| 7,225,013 B2 | 5/2007 | Geva et al. |
| 7,314,451 B2 | 1/2008 | Halperin |
| 7,359,837 B2 | 4/2008 | Drew |
| 7,572,225 B2 | 8/2009 | Stahmann et al. |
| 7,578,794 B2 | 8/2009 | Hatlestad et al. |
| 7,766,842 B2 | 8/2010 | Ni et al. |
| 7,931,600 B2 | 4/2011 | Hatlestad et al. |
| 7,983,745 B2 | 7/2011 | Hatlestad et al. |
| 2002/0151812 A1 | 10/2002 | Scheiner et al. |
| 2002/0161412 A1 | 10/2002 | Sun et al. |
| 2002/0188213 A1 | 12/2002 | Bardy |
| 2002/0193697 A1 | 12/2002 | Cho et al. |
| 2002/0193839 A1 | 12/2002 | Cho et al. |
| 2003/0023184 A1 | 1/2003 | Pitts-Crick et al. |
| 2003/0055461 A1 | 3/2003 | Girouard et al. |
| 2003/0100925 A1 | 5/2003 | Pape et al. |
| 2003/0105497 A1 | 6/2003 | Zhu et al. |
| 2003/0139780 A1 | 7/2003 | Markowitz et al. |
| 2003/0153953 A1 | 8/2003 | Park et al. |
| 2003/0153954 A1 | 8/2003 | Park et al. |
| 2003/0153955 A1 | 8/2003 | Park et al. |
| 2003/0153956 A1 | 8/2003 | Park et al. |
| 2003/0163059 A1 | 8/2003 | Poezevera et al. |
| 2004/0002742 A1 | 1/2004 | Florio |
| 2004/0030362 A1 | 2/2004 | Hill et al. |
| 2004/0059240 A1 | 3/2004 | Cho et al. |
| 2004/0088027 A1 | 5/2004 | Burnes et al. |
| 2004/0102814 A1 | 5/2004 | Sorensen et al. |
| 2004/0111040 A1 | 6/2004 | Ni et al. |
| 2004/0116981 A1 | 6/2004 | Mazar |
| 2004/0122487 A1 | 6/2004 | Hatlestad et al. |
| 2004/0122488 A1 | 6/2004 | Mazar et al. |
| 2004/0127807 A1 | 7/2004 | Hatlestad et al. |
| 2004/0128161 A1 | 7/2004 | Mazar et al. |
| 2004/0133079 A1 | 7/2004 | Mazar et al. |
| 2004/0138719 A1 | 7/2004 | Cho et al. |
| 2005/0043772 A1 | 2/2005 | Stahmann et al. |
| 2005/0080348 A1 | 4/2005 | Stahmann et al. |
| 2006/0085038 A1 | 4/2006 | Linder et al. |
| 2006/0241510 A1 | 10/2006 | Halperin et al. |
| 2007/0088399 A1 | 4/2007 | Linder et al. |
| 2009/0177702 A1 | 7/2009 | Stahmann et al. |

OTHER PUBLICATIONS

File History for U.S. Appl. No. 11/236,192.
File History for U.S. Appl. No. 12/545,652.
File History for U.S. Appl. No. 12/403,880.
File History for EP Application No. 03808539.5 as retrieved from the European Patent Office Electronic File System on Apr. 26, 2011, 122 pages.
Office Action dated Dec. 14, 2009 from Japanese Application No. 2004-565641, 3 pages.
Office Action dated Aug. 16, 2010 from Japanese Application No. 2004-565641, 2 pages.
Balaban et al., Feasibility of Screening for Sleep Apnea Using Pacemaker Impedance Sensor, NASPE (2001).
Bradley et al., Pathophysiologic and Therapeutic Implications of Sleep Apnea in Congestive Heart Failure, 3 J. Cardiac Failure 223-240 (1996).
Bradley et al., Sleep Apnea and Heart Failure, Part I: Obstructive Sleep Apnea, 107 Circulation 1671-1678 (2003).
Cowie et al., Survival of Patients with a New Diagnosis of Heart Failure: A Population Based Study, Heart 2000; 83:505-510.
Garrigue et al., Night Atrial Overdrive with DDD Pacing: a New Therapy for Sleep Apnea Syndrome, NASPE (2000).
Garrigue et al., Night Atrial Overdrive with DDD Pacing Results in a Significant Reduction of Sleep Apnea Episodes and QOL Improvement in Heart Failure Patients, NASPE (2001).

(56) References Cited

OTHER PUBLICATIONS

Garrigue et al., Benefit of Atrial Pacing in Sleep Apnea Syndrome, 346 N. Engl. J. Med. 404-412 (2002).

Guidant System Guide, Vitality AVT™, Automatic Implantable Cardioverter Defibrillator Model A135, Part 1 of 2, Chapter 7, pp. 7-1 through 7-30, 2003.

Hilton et al., Evaluation of Frequency and Time-frequency Spectral Analysis of Heart Rate Variability as a Diagnostic Marker of the Sleep Apnea Syndrome, 37 Med. Biol. Eng. Comput. 760-769 (1999). Abstract only.

Javaheri et al., Sleep Apnea in 81 Ambulatory Male Patients with Stable Heart Failure: Types and Their Prevalences, Consequences, and Presentations, 97 Circulation 2154-2159 (1998).

Javaheri et al., A Mechanism of Central Sleep Apnea in Patients With Heart Failure, 341 N. Engl. J. Med. 949-954 (1999).

Lehrer, Understanding Lung Sounds, Second Ed., Copyright 1993, 1984 by W.B. Saunders Company, pp. 91-105.

Saul, Respiratory Sinus Arrhythmia, Vagal Control of the Heart: Experimental Basis and Clinical Implications edited by M.N. Levy, P.J. Schwartz, copyright 1994, Futura Publishing Co., In., Armonk, NY, pp. 511-537.

Vanninen et al., Cardiac Sympathovagal Balance During Sleep Apnea Episodes, 16 Clin. Physiol. 209-216 (1996).

Young et al., The Occurrence of Sleep-Disordered Breathing Among Middle Aged Adults, N. Engl. J. Med. 1230-1235 (1993).

File History for U.S. Appl. No. 13/094,597.

Notice of Allowance dated Jul. 28, 2009 from U.S. Appl. No. 11/121,450, 4 pages.

Office Action Response dated Jun. 16, 2009 from U.S. Appl. No. 11/121,450, 9 pages.

Interview Summary dated Jun. 9, 2009 from U.S. Appl. No. 11/121,450, 2 pages.

Office Action dated Apr. 27, 2009 from U.S. Appl. No. 11/121,450, 3 pages.

Office Action Response dated Apr. 16, 2009 from U.S. Appl. No. 11/121,450, 8 pages.

Office Action dated Feb. 17, 2009 from U.S. Appl. No. 11/121,450, 7 pages.

Office Action Response dated Dec. 9, 2008 from U.S. Appl. No. 11/121,450, 8 pages.

Office Action dated Jul. 9, 2008 from U.S. Appl. No. 11/121,450, 7 pages.

Office Action Response dated Jun. 9, 2008 from U.S. Appl. No. 11/121,450, 7 pages.

Office Action dated Mar. 3, 2008 from U.S. Appl. No. 11/121,450, 7 pages.

Office Action Response dated Dec. 10, 2007 from U.S. Appl. No. 11/121,450, 8 pages.

Office Action dated Aug. 6, 2007 from U.S. Appl. No. 11/121,450, 7 pages.

Office Action Response dated May 25, 2007 from U.S. Appl. No. 11/121,450, 9 pages.

Office Action dated Feb. 21, 2007 from U.S. Appl. No. 11/121,450, 12 pages.

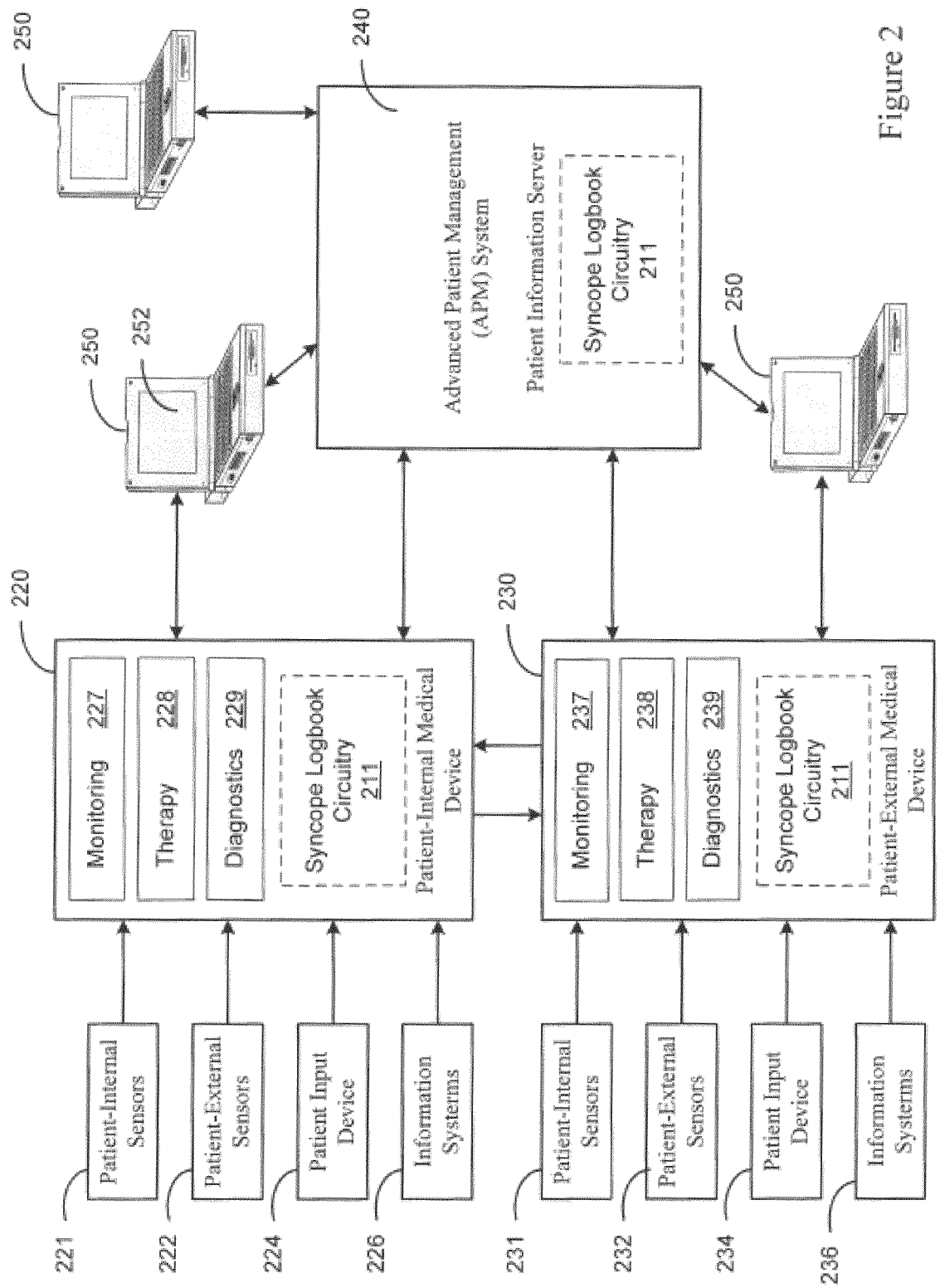

SYNCOPE LOGBOOK AND METHOD OF USING SAME

RELATED APPLICATIONS

This application is a continuation of U.S. patent application Ser. No. 11/121,450, filed on May 4, 2005, which is incorporated herein by reference.

FIELD OF THE INVENTION

The present invention relates to acquiring and organizing information related to syncope events.

BACKGROUND OF THE INVENTION

The human body functions through a number of interdependent physiological systems controlled through various mechanical, electrical, and chemical processes. The metabolic state of the body is constantly changing. For example, as exercise level increases, the body consumes more oxygen and gives off more carbon dioxide. The cardiac and pulmonary systems maintain appropriate blood gas levels by making adjustments that bring more oxygen into the system and dispel more carbon dioxide. The cardiovascular system transports blood gases to and from the body tissues. The respiratory system, through the breathing mechanism, performs the function of exchanging these gases with the external environment. Together, the cardiac and respiratory systems form a larger anatomical and functional unit denoted the cardiopulmonary system.

Various disorders may affect the cardiovascular, respiratory, and other physiological systems. For example, heart failure is a clinical syndrome that impacts a number of physiological processes. Heart failure is an abnormality of cardiac function that causes cardiac output to fall below a level adequate to meet the metabolic demand of peripheral tissues and internal organs. Heart failure is often referred to as congestive heart failure (CHF) due to the accompanying venous and pulmonary congestion. Congestive heart failure may have a variety of underlying causes, including ischemic heart disease (coronary artery disease), hypertension (high blood pressure), and diabetes, among others.

There are a number of diseases and disorders that primarily affect respiration, but also impact other physiological systems. Emphysema and chronic bronchitis are grouped together and are known as chronic obstructive pulmonary disease (COPD). Pulmonary system disease also includes tuberculosis, sarcoidosis, lung cancer, occupation-related lung disease, bacterial and viral infections, and other conditions.

Chronic obstructive pulmonary disease generally develops over many years, typically from exposure to cigarette smoke, pollution, or other irritants. Over time, the elasticity of the lung tissue is lost, and the lungs become distended, unable to expand and contract normally. As the disease progresses, breathing becomes labored, and the patient grows progressively weaker. Other types of non-rhythm related pulmonary diseases or disorders include restrictive pulmonary diseases, infections pulmonary diseases, diseases of the pleural cavity, and pulmonary vasculature, for example.

Breathing disorders include various forms of rhythm-related disorders such as sleep apnea and hypopnea, among other forms. Disordered breathing is a respiratory system condition that affects a significant percentage of patients between 30 and 60 years. Disordered breathing, including apnea and hypopnea, may be caused, for example, by an obstructed airway, or by derangement of the signals from the brain controlling respiration. Disordered breathing occurs when a patient experiences insufficient respiration with or without respiratory effort. Disordered breathing can originate from a deficiency in the central nervous system (central disordered breathing) or from an obstructed airway (obstructive disordered breathing). Lack of respiratory effort may result from a disruption of signals from the central nervous system to the respiratory muscles.

Syncope, pre-syncope, and falls are events that may occur in conjunction with disorders affecting the cardiovascular, respiratory, and other physiological systems. Syncope is caused by temporary reduction or loss of blood flow to areas of the brain necessary for consciousness. The frequency of occurrence and conditions preceding a patient's syncopal events is often unclear because a patient may be unaware of the syncope event, unable to recall conditions preceding the event and/or no witnesses were present for the event. As a result, a large percentage of patients suffering from syncope disorders go undiagnosed. Patients suffering from syncope events can benefit from monitoring to determine the occurrence and origin of syncope events in order to provide an effective diagnosis and treatment for such events.

Recording data associated with syncope-related events can assist physicians in diagnosing and treating syncope. In the past, patient conditions related to syncope have been tested and observed in controlled environments by conducting tests such as blood tests, X-rays, 24-hour Holter monitoring, tilt table tests, and/or treadmill tests. Syncope-related events, however, are transient in nature and merely observing a patient for a short period of time or subjecting a patient to tests may not produce adequate syncope event information for diagnosis or therapy.

SUMMARY OF THE INVENTION

Embodiments of the invention are directed to methods and systems for acquiring and organizing information related to syncope events.

In accordance with one embodiment, an automated method is used to collect and organize information associated with at least one syncope event. A syncope event may comprise a suspected syncope event, a verified syncope event or a syncope event that is suspected and verified. Information associated with at least one syncope event is acquired. The information is organized as a syncope log entry. At least one of acquiring the information and organizing the information is performed at least in part implantably.

In accordance with various aspects of the invention, information associated with at least one syncope event may be acquired from sensed cardiovascular system parameters and/or respiration signal parameters.

In accordance with another aspect of the invention, information associated with at least one syncope event is acquired in response to a triggering event.

In a further embodiment of the invention, a medical system, which may be fully or partially implantable, includes a data acquisition unit used to acquire information associated with at least one syncope event. The syncope event may be a suspected syncope event, a verified syncope event or a suspected and verified syncope event. The medical system further includes a processor coupled to the data acquisition unit. The processor organizes acquired information as syncope event log entries.

The above summary of the invention is not intended to describe each embodiment or every implementation of the invention. Advantages and attainments, together with a more complete understanding of the invention, will become apparent and appreciated by referring to the following detailed description and claims taken in conjunction with the accompanying drawings.

BRIEF DESCRIPTION OF THE DRAWINGS

FIG. 2 is a block diagram illustrating a medical system including a patient-internal device and/or a patient-external device used to acquire and organize information in a syncope logbook in accordance with embodiments of the invention;

Figure 1:
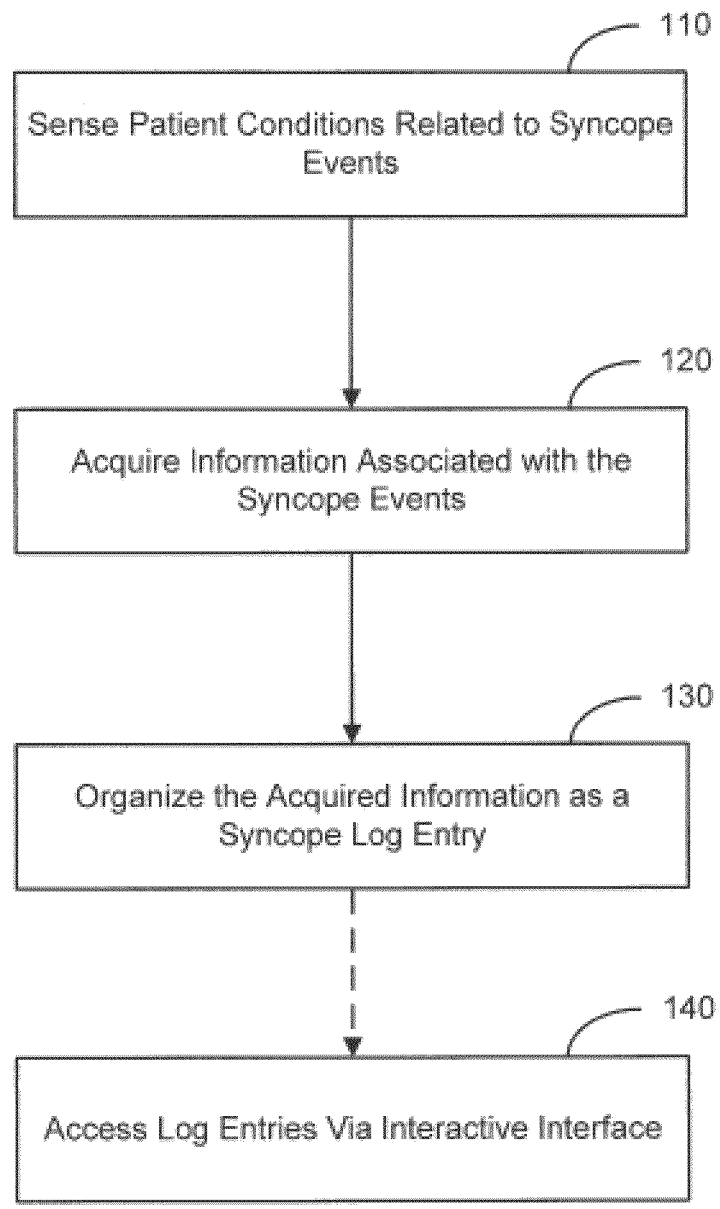
FIG. 1 is a flowchart illustrating a method of acquiring and organizing patient information collected in response to a syncope-related event.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings that form a part hereof, and in which is shown by way of illustration, various embodiments in which the invention may be practiced. It is to be understood that other embodiments may be utilized and structural and functional changes may be made without departing from the scope of the present invention.

Early detection and diagnosis of various types of conditions related to patient diseases and syndromes may enhance the likelihood of successful treatment. However, the onset of some conditions related to medical disorders may be very gradual and/or occur in discrete episodes, or at times that are inconvenient for collecting data, making early detection more difficult. Early diagnosis may depend on the recognition of changes in various physiological conditions that may not be apparent during yearly or even monthly check-ups.

Syncope can have a variety of origins including cardiovascular, respiratory, neurological and/or vasovagal origins, for example. Information related to patient conditions or parameters before, during, and/or after syncope, presyncope or fall event aids in diagnosis and treatment. However, the intermittent nature of such events complicates acquisition of the information.

Embodiments of the invention are directed to an event-based approach to storing and organizing information associated with events related to syncope. The term "syncope" may comprise, for example, syncope, pre-syncope and/or falls. Further, a syncope event or syncope-related event may comprise a suspected syncope event, such as a suspected syncope event or a suspected fall, and/or a verified syncope event. In one implementation, various types of information acquired during time intervals surrounding a syncope-related event, including physiological and/or non-physiological information, is organized into a logbook entry. The information acquired may be any type of information useful in the detection, monitoring, diagnosis, and/or treatment of syncope-related events, for example.

FIG. 1 is a flowchart illustrating a method of acquiring and organizing patient information collected in response to a syncope-related event. In accordance with embodiments of the invention, conditions affecting the patient and associated with a syncope-related event are sensed 110 and information associated with the event is acquired 120 based on the sensed conditions. The acquired information is organized 130 as a syncope event log entry. Sensing, acquiring, and/or organizing the syncope-related event information can be performed using one or more devices that are fully or partially implanted within a patient.

In one implementation, the logbook entry may be organized, along with other logbook entries, in a syncope logbook that is stored in the memory of a computing device. The syncope logbook may be stored in a patient implantable device or a patient external device. The stored syncope logbook entries may be optionally accessible 140 through an interactive user interface.

FIG. 2 is a block diagram of a medical system that may be used to implement a syncope logbook system in accordance with embodiments of the invention. The medical system may include, for example, one or more patient-internal medical devices 220 and one or more patient-external medical devices 230. Each of the patient-internal 220 and patient-external 230 medical devices may include one or more of a patient monitoring unit 227, 237, a diagnostics unit 229, 239, and/or a therapy unit 228, 238. Components of the syncope logbook 211 can be part of a patient internal medical device 220, a patient external medical device 230, a remote network server system such as advanced patient management (APM) system 240 or any combination of the above-mentioned devices 220, 230, 240.

The patient-internal medical device 220 may be a fully or partially implantable device that performs monitoring, diagnosis, and/or therapy functions. The patient-external medical device 230 may perform monitoring, diagnosis and/or therapy functions external to the patient (i.e., not invasively implanted within the patient's body). The patient-external medical device 230 may be positioned on the patient, near the patient, or in any location external to the patient. It is understood that a portion of a patient-external medical device 230 may be positioned within an orifice of the body, such as the nasal cavity or mouth, yet can be considered external to the patient (e.g., mouth pieces/appliances, tubes/appliances for nostrils, or temperature sensors positioned in the ear canal).

The patient-internal and patient-external medical devices 220, 230 may be coupled to one or more sensors 221, 222, 231, 232, patient input devices 224, 234 and/or other information acquisition devices 226, 236. The sensors 221, 222, 231, 232, patient input devices 224, 234, and/or other information acquisition devices 226, 236 may be employed to detect conditions relevant to the monitoring, diagnostic, and/or therapeutic functions of the patient-internal and patient-external medical devices 220, 230.

The medical devices 220, 230 may each be coupled to one or more patient-internal sensors 221, 231 that are fully or partially implantable within the patient. The medical devices 220, 230 may also be coupled to patient-external sensors 222, 232 positioned on the patient, near the patient, or in a remote location with respect to the patient. The patient-internal 221, 231 and patient-external 222, 232 sensors may be used to sense conditions, such as physiological or environmental conditions, that affect the patient.

The patient-internal sensors 221 may be coupled to the patient-internal medical device 220 through implanted leads. In one example, an internal endocardial lead system is used to couple sensing electrodes to an implantable pacemaker, neural stimulator or other cardiac rhythm management device. One or more of the patient-internal sensors 221, 231 may be equipped with transceiver circuitry to support wireless communication between the one or more patient-internal sensors 221, 231 and the patient-internal medical device 220 and/or the patient-external medical device 230.

The patient-external sensors 222, 232 may be coupled to the patient-internal medical device 210 and/or the patient-external medical device 220 through leads or through wireless connections. Patient-external sensors 222 preferably communicate with the patient-internal medical device 220 wirelessly. Patient-external sensors 232 may be coupled to the patient-external medical device 230 through leads or through a wireless link.

The medical devices 220, 230 may be coupled to one or more patient-input devices 224, 234. The patient-input devices 224, 234 facilitate manual transfer of information to the medical devices 220, 230 by the patient. The patient input devices 224, 234 may be particularly useful for inputting information concerning patient perceptions, such as how well the patient feels, and patient-known information such as patient smoking, drug use, or other activities that are not automatically sensed or detected by the medical devices 220, 230. In one implementation, a device programmer may be used to facilitate patient input to a medical device 220, 230.

The medical devices 220, 230 may be connected to one or more information systems 226, 236, for example, a database that stores information useful in connection with the monitoring, diagnostic, or therapy functions of the medical devices 220, 230. In one implementation, one or more of the medical devices 220, 230 may be coupled through a network to an information system server that provides information about environmental conditions affecting the patient, e.g., the pollution index for the patient's location.

In one embodiment, the patient-internal medical device 220 and the patient-external medical device 230 may communicate through a wireless link between the medical devices 220, 230. For example, the patient-internal and patient-external devices 220, 230 may be coupled through a short-range radio link, such as Bluetooth or a wireless link. The communications link may facilitate uni-directional or bi-directional communication between the patient-internal 220 and patient-external 230 medical devices. Data and/or control signals may be transmitted between the patient-internal 220 and patient-external 230 medical devices to coordinate the functions of the medical devices 220, 230.

In one embodiment, the patient-internal and patient-external medical devices 220, 230 may be used within the structure of an advanced patient management system. Advanced patient management systems involve a system of medical devices that are accessible through various communications technologies. For example, patient data may be downloaded from one or more of the medical devices periodically or on command, and stored at a patient information server. The physician and/or the patient may communicate with the medical devices and the patient information server, for example, to acquire patient data or to initiate, terminate or modify therapy.

The patient-internal medical device 220 and the patient-external medical device 230 may be coupled through a wireless or wired communications link to a patient information server that is part of an advanced patient management system 240. The APM patient information server 240 may be used to download and store data collected by the patient-internal and patient-external medical devices 220, 230.

The data stored on the APM patient information server 240 may be accessible by the patient and the patient's physician through terminals 250, e.g., remote computers located in the patient's home or the physician's office. The APM patient information server 240 may be used to communicate to one or more of the patient-internal and patient-external medical devices 220, 230 to effect remote control of the monitoring, diagnosis, and/or therapy functions of the medical devices 220, 230.

In one scenario, the patient's physician may access patient data transmitted from the medical devices 220, 230 to the APM patient information server 240. After evaluation of the patient data, the patient's physician may communicate with one or more of the patient-internal or patient-external devices 220, 230 through the APM system 240 to initiate, terminate, or modify the monitoring, diagnostic, and/or therapy functions of the patient-internal and/or patient-external medical systems 220, 230. Systems and methods involving advanced patient management techniques are further described in U.S. Pat. Nos. 6,336,903, 6,312,378, 6,270,457, and 6,398,728 which are incorporated herein by reference.

In one scenario, the patient-internal and patient-external medical devices 220, 230 may not communicate directly with each other, but may communicate indirectly through the APM system 240. In this embodiment, the APM system 240 may operate as an intermediary between two or more of the medical devices 220, 230. For example, data and/or control information may be transferred from one of the medical devices 220, 230 to the APM system 240. The APM system 240 may transfer the data and/or control information to another of the medical devices 220, 230.

As previously indicated, syncope logbook circuitry 211, including an external device interface, event detector/predictor, event information processor and memory, for example, can be housed in a patient internal medical device 220, a patient external medical device 230, an advanced patient medical (APM) system 240 or in any combination of the above-mentioned devices. For explanatory purposes, in the following discussion, the syncope logbook circuitry 211 is described as being housed within the patient internal medical device 220. As previously discussed, the patient internal medical device 220 may be coupled to various sensors, 221, 222, patient input devices 224, and/or other information systems 226. These sensing and detection devices may be used to detect conditions affecting the patient that are associated with syncope-related events.

In accordance with various embodiments of the invention, the syncope logbook 211 may comprise circuitry configured to evaluate one or more patient conditions to detect or predict the occurrence of a syncope-related event. In response to the detection or prediction of such an event, the syncope logbook circuitry initiates the collection of information related to the event. In one scenario, the syncope logbook circuitry may initiate collection of information from sensors 221, 231, 222, 232 or other input devices 224, 234, 226, 236 coupled to any combination of the patient internal medical device, 220 patient external medical device 230 and a remote device, such as the APM server 240.

Information associated with syncope-related events may be acquired before, during and/or after the event. Information may be acquired for a time period beginning a short time, e.g., up to about 5 minutes, prior to the prediction and/or detection of a syncope-related event and/or ending a short time, e.g., up to about 2 minutes, following the termination of the syncope-related event. In some embodiments, the acquired information may be stored in the patient-internal device 220 for later transfer to a computing device 230, 240, 250. The information may be organized and displayed on a display unit 252, for example.

information related to syncope logbook events. The acquired information may include both physiological and non-physiological or contextual conditions affecting the patient. Physiological conditions may include a broad category of conditions associated with the internal functioning of the patient's physiological systems, including the cardiovascular, respiratory, nervous, muscle and other systems. Examples of physiological conditions include blood chemistry, patient posture, patient activity, respiration quality, sleep quality, among others. Examples of non-physiological conditions affecting the patient and associated with syncope-related events may include, for example, pollution index, ambient temperature and/or humidity. Tables 1-2 provide a non-exhaustive, illustrative list of conditions affecting the patient associated with syncope-related events.

TABLE 1

| Condition Type | | Condition | Sensor type or Detection method |
|---|---|---|---|
| Physiological | Cardiovascular System | Heart rate | EGM, ECG |
| | | Heart rate variability | |
| | | QT interval | |
| | | Ventricular filling pressure | Intracardiac pressure sensor |
| | | Blood pressure | Blood pressure sensor |
| | Respiratory System | Respiration pattern (Tidal volume Minute ventilation Respiratory rate) | Transthoracic impedance sensor (AC) |
| | | Pulmonary congestion | Transthoracic impedance sensor (DC) |
| | Nervous System | Brain activity | EEG |
| | | Autonomic neural traffic | Peripheral nerve sensor |
| | Blood Chemistry | $CO_2$ saturation | Blood analysis |
| | | $O_2$ saturation | |
| | | Blood alcohol content | |
| | | Adrenalin | |
| | | Blood glucose level | |
| | | Drug/Medication/Tobacco use | |
| Contextual | Environmental | Patient activity | Accelerometer, MV, etc. |
| | | Humidity | Hygrometer |
| | | Pollution | Air quality website |
| | | Time | Clock |
| | | Posture | Multi-axis accelerometer |
| | | Altitude | Altimeter |
| | | Location | GPS, proximity sensor |
| | Historical/Background | Age | Patient input |
| | | Recent exercise | |
| | | Weight | |
| | | Gender | |
| | | Body mass index | |
| | | Medical history | |
| | | Emotional state | |
| | | Psychological history | |
| | | Drug, alcohol, nicotine use | |

The patient-internal sensors 221, 231, patient-external sensors 222, 232, patient input devices 224, 234, and/or information systems 226, 236 may be used to acquire a variety of Table 2 provides examples of how a representative subset of the physiological and contextual conditions listed in Table 1 may be used in connection with syncope detection.

TABLE 2

| Condition Type | Condition | Examples of how condition may be used in syncope detection |
|---|---|---|
| Physiological | Heart rate | Decrease in heart rate may indicate cardiac-originated syncope. Increase in heart rate may indicate arousal from cardiac-originated syncope. |

TABLE 2-continued

| Condition Type | Condition | Examples of how condition may be used in syncope detection |
|---|---|---|
| | Ventricular filling pressure | May be used to identify/predict pulmonary congestion associated with cardiac-originated syncope. |
| | Blood pressure | Sudden change in blood pressure measures are associated with syncope. |
| | Respiration pattern/rate | Respiration patterns including, e.g., respiration rate, may be used to detect syncope. |
| | Pulmonary congestion | Pulmonary congestion is associated with syncope. |
| | Blood glucose level | Low blood sugar can trigger the onset of syncope. |
| | Adrenalin | End of syncope associated with a spike in blood adrenaline. |
| | Drug/Medication/ Tobacco use | These substances may affect the incidence of syncope. |
| | Activity | Patient activity may be used in relation to syncope detection. |
| | Posture | Posture may be used to confirm or determine whether the patient is standing or sitting. Rapid postural changes are often associated with postural hypotension and syncope. |
| Contextual | Humidity | Humidity may be a condition predisposing the patient to respiratory-originated syncope and may be useful respiratory-originated syncope detection. |
| | Pollution | Pollution may be a condition predisposing the patient to respiratory-originated syncope and may be useful in syncope detection. |
| | Altitude | Lower oxygen concentrations at higher altitudes tends to cause respiratory-originated syncope events. |

Syncope-related events may involve various types of events affecting one or more of the respiratory system, cardiovascular system, nervous system, muscle systems, and/or other physiological systems or combinations of physiological systems of the patient. An implantable device, such as a cardiac pacemaker or other cardiac rhythm management (CRM) device, may be used to facilitate long-term monitoring of syncope-related events and implementation of a syncope logbook.

In some implementations, sensor systems employed by implantable CRM devices may be used to detect patient parameters associated with syncope, pre-syncope and/or falls. For example, the intracardiac or extracardiac sensors coupled to a CRM device may be used to acquire important cardiac information associated with syncope. The CRM device may incorporate one or more electrogram sensors used to sense cardiac electrical activity, including ventricular and/or atrial electrograms. Cardiac electrical activity information may be used to determine if the syncope has an origin related to cardiac arrhythmia, such as AV block, Stokes-Adams attack, or paroxysmal atrial tachycardia.

In addition to electrogram sensors, a CRM device may incorporate other sensors useful in monitoring syncope-related events. For example, a blood pressure sensor and/or cardiac output sensor can gather data indicating the presence of a syncope-related event associated with irregularies of the cardiovascular system. A transthoracic impedance sensor may be incorporated within a CRM device and used to determine various respiratory system parameters, including, for example, respiration rate, tidal volume, and minute ventilation. Transthoracic impedance sensing may be used to detect parameters associated with the occurrence of syncope such as hypoventilation, hyperventilation and/or coughing. Alternatively, or additionally, respiratory system conditions can be detected using sensors of an external respiratory device, such as, for example, a continuous positive airway pressure (CPAP) device, bi-level positive airway pressure device (bi-PAP) or other device.

Patient conditions associated with and/or triggering syncope-related events and the sensors/devices used to sensor or detect the patient conditions may include, for example, the one or a combination of the following:

Hypoglycemia can trigger the onset of a syncope-related event and may be sensed using a patient-internal blood glucose sensor.

A posture sensor can provide information indicating orthostatic syncope.

An implanted or patient external accelerometer can detect syncope having a variety of origins by detecting a sudden change in activity.

Abnormal changes in the DC value of the transthoracic impedance signal upon change of posture may also indicate a pre-syncopal condition.

Falls, which can be syncope-related, can be detected by monitoring accelerometer and/or posture sensor signals for patterns unique to an abrupt fall.

A patient can also identify when the onset of a syncope-related event occurred. When the patient detects the syncope-related event the patient can manually log the event into a system in accordance with the present invention with a "patient input" device. The device can be located, for example, on a station, with a keyboard and transmitter, on a wearable device such as a watch, or can be a simple magnet device that can interact with the implantable device.

It will be appreciated that patient conditions and detection methods other than those listed in Tables 1-2 or listed above may be used in connection with detecting syncope-related events and are considered to be within the scope of the invention.

In embodiments of the present invention, acquisition of information associated a syncope-related event (syncope, pre-syncope or fall) can take place during the syncope-related event and during time periods proximate to the event, e.g., before and/or after the event. In some implementations, the patient conditions may be used to predict the occurrence of the syncope-related event. In these implementations, acquisition of the information may occur prior to and/or after the prediction or detection of the event, as well as during the event.

To facilitate acquiring medical information associated with syncope-related events, patient conditions may be monitored, e.g., on a continuous or periodic basis, and stored in a temporary buffer. Temporary storage is required to provide information prior to the event prediction or detection, e.g., onset data. The size of the temporary storage buffer may vary according to the medical events for which onset data is desired. Due to the varied nature of onset data requirements and the reality of limited storage in the system, the system may allow different onset data lengths and different sampling rates for the temporarily stored data. In the preferred embodiment the system would use a circular buffer to store the temporary data such that the oldest data is replaced by the newest data.

Once initiated, acquisition of syncope-related event information, which may involve storage of the information in long term memory, may be performed on a substantially continuous basis, or it may be performed periodically. Long term storage of data acquired periodically may be beneficial when the event is relatively prolonged. The type of data collected, data collection frequency, and/or data collection intervals may be selectable by the user. Further, the system may be programmable to use different data collection regimens under different conditions over the course of the event. For example, the system may be programmable to collect data during a patient's wakeful period, for example. The system may be programmed to collect data on a continuous basis during some time intervals, and periodically during other time intervals, for example.

Acquiring information preceding the event facilitates enhanced identification of conditions that may be used to detect or predict the occurrence of future events. For example, acquiring information preceding a syncope-related event allows for the identification and assessment of physiological conditions present immediately before and leading up to the event. The identification of precursor conditions for syncope-related events may facilitate increased sensitivity and/or accuracy in detecting or predicting occurrences of the future events.

Various types of syncope-related information can be acquired and stored including: episode number, time of day, heart electrograms (pre-event, during the event and post-event), leadless ECGs, heart rate (intrinsic and paced), electrical therapy (pacing and/or shocks), cardiac output, respiration rate, respiration rate baseline, respiration waveform (pre-event, during the event and post-event), tidal volume, tidal volume baseline, minute ventilation, minute ventilation baseline, inspiration/expiration ratio, xPAP therapy (pressure level), coughing, syncope event origin, syncope event duration, syncope event severity, patient activity, patient posture, pulmonary congestion, blood pressure, blood gas ($O_2$ and $CO_2$), blood glucose level, autonomic tone, baroreceptor response, DC impedance, and arrhythmia information for example.

In some embodiments of the invention, one or more conditions may be used to trigger the acquisition of syncope-related information. A triggering event for acquiring information related to a syncope episode may be, for example, a condition predisposing the patient to syncope-related events, a condition known or suspected to be a precursor condition for syncope-related events, and/or a condition indicative of the occurrence of a syncope-related event. Each type of syncope, pre-syncope or fall event, e.g., cardiac-originated event and respiratory-originated event, may be associated with a separate set of trigger sensors. A manual trigger that can be set by a patient can be implemented in embodiments of the invention. Patient control of a trigger for acquiring information related to syncope allows the patient to set the trigger when the patient notices symptoms of syncope occurring. Coughing and or breathing irregularities associated with pulmonary edema, chronic obstructive pulmonary disease (COPD), asthma and plural effusion can be a trigger for acquiring information related to syncope. Using conditions predisposing the patient to syncope-related events and/or precursor conditions to syncope-related events as triggers for acquiring syncope episode information allows data to be gathered related to the period of time just before the syncope event occurs.

The condition or conditions used to trigger the initiation of data collection exhibits a detectable or predictable change caused by an impending syncope event preceding, or coincident with, the beginning of the syncope event. The one or more conditions used to trigger the end of data collection exhibit a detectable change coincident with or shortly after the end of a syncope event. Acquiring information associated with syncope-related events may end upon detecting a trigger-off event, or data collection may continue for a selected period of time following the trigger-off event.

The acquired patient information is organized as a syncope event log entry. A syncope event logbook may comprise a number of entries, each entry corresponding to a separate syncope-related event. The event entries included in syncope logbook may be organized according to various categories, including for example, event type, event time/date, severity, order of occurrence of the event, therapy provided to treat the event, among other categories. The selection of categories used to organize the information may be programmable by the user. The organized information may be stored in long term memory, displayed, printed, and/or transmitted to a separate device. Storing patient information in discrete segments allows storage space to be allocated specifically to syncope episodes.

In some embodiments of the invention, the acquired information for the events is optionally accessible through an interactive user interface. Selection of events to be accessed may involve a hierarchical selection menu, or other selection method, for example. In one implementation, the user may select a log entry from the menu by activating an input mechanism. Upon selection of the log entry, the user interface may provide graphical or textual depictions of the collected patient information associated with the medical event.

Event information of the logbook may be stored in long term memory using various storage methodologies. For example, the logbook may utilize a flat file system, hierarchical database, relational database, or distributed database. Data for a group of events may be analyzed and/or summarized in various formats. Graphical and/or textual summary information may be displayed on the user interface and/or otherwise communicated to the user. For example, histograms, trend graphs, and/or other analytical tools or formats may be generated based on the logbook event entries.

Figure 3A:
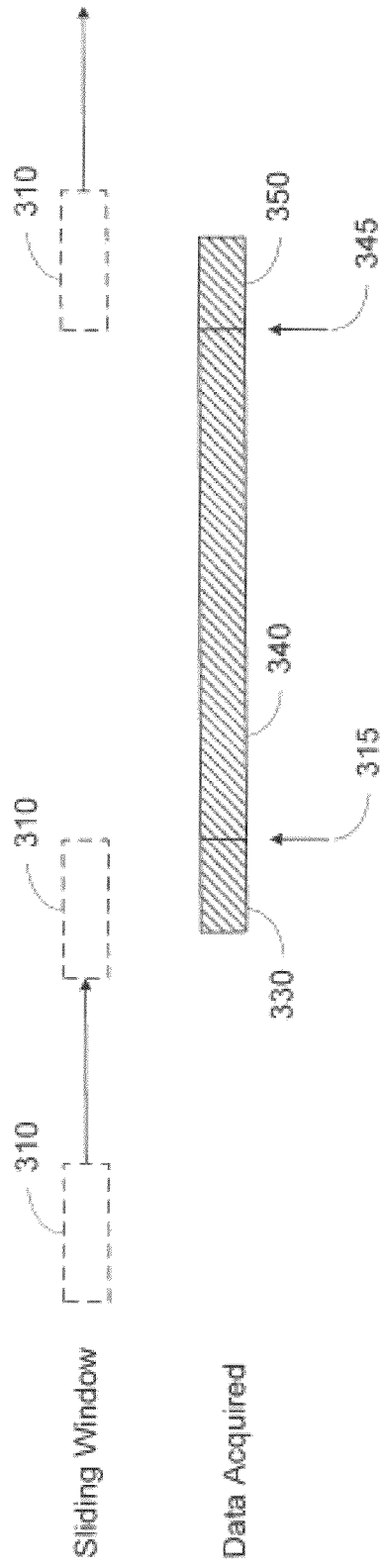
FIG. 3A provides a timing diagram illustrating the acquisition of syncope logbook information for a detected event affecting the patient in accordance with embodiments of the invention.

FIG. 3A provides a timing diagram illustrating the acquisition of syncope logbook information for a detected event affecting the patient in accordance with embodiments of the invention. The syncope logbook system senses and stores in a temporary buffer a sliding scale window 310 of one or more patient conditions, such as those listed in Tables 1-2. The selection of information that is sensed and stored may be programmable by the physician. The selection of the information to be acquired may be based on the patient's medical history. For example, if the patient suffers from syncope predominantly originating from the respiratory system, syncope logbook would preferably be programmed to sense conditions associated with disordered breathing. Conversely, if the patient suffers from cardiac originated syncope, a different set of conditions focused on cardiac functioning could be sensed.

If a syncope-related event is detected 315, then pre-event information 330 acquired prior to the event is stored. Information is collected and stored during 340 the event. Upon detection that the event has terminated 345, post-event information 350 is collected and stored for a period of time after the termination of the event. The event and post-event information 340, 350 may be acquired on a continuous basis, or the information may be acquired during discrete intervals. After the post-event information 350 is collected, the acquired information 330, 340, 350 is organized as a logbook entry. The syncope logbook system begins sensing for the next event.

Figure 3B:
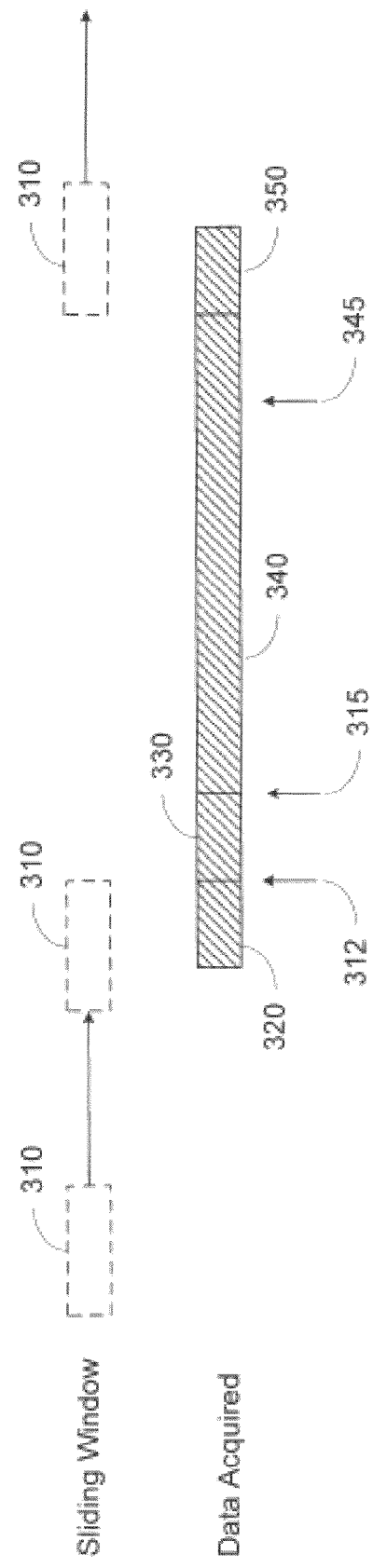
FIG. 3B provides a timing diagram illustrating the acquisition of syncope logbook information for a predicted event affecting the patient in accordance with embodiments of the invention.

FIG. 3B provides a timing diagram illustrating the acquisition of syncope logbook information for a predicted event affecting the patient in accordance with embodiments of the invention. The syncope logbook system senses and stores in a temporary buffer a sliding scale window 310 of one or more patient conditions, such as those listed in Tables 1-2. The conditions that are sensed and stored are programmable and may be selected based on the patient's medical history. For example, the information sensed and stored may include information that has been effectively used to predict the one or more types of events leading to pre-syncope, syncope or falls. If a syncope-related event is predicted 312, then pre-prediction information 320 is acquired and stored. When the syncope-related event is detected 315, then pre-event information 330 acquired prior to the event is stored. Information 340 is collected and stored during the event. Upon detection that the event has terminated 345, information 350 is collected and stored for a period of time after the termination of the event. The pre-event, event and post-event information 330, 340, 350 may be acquired on a continuous basis, or the information may be acquired during discrete intervals. After the post-event information 340 is collected, the acquired information 320, 330, 340, 350 is organized as a logbook entry and the syncope logbook circuitry begins sensing for the next event.

Figure 4:
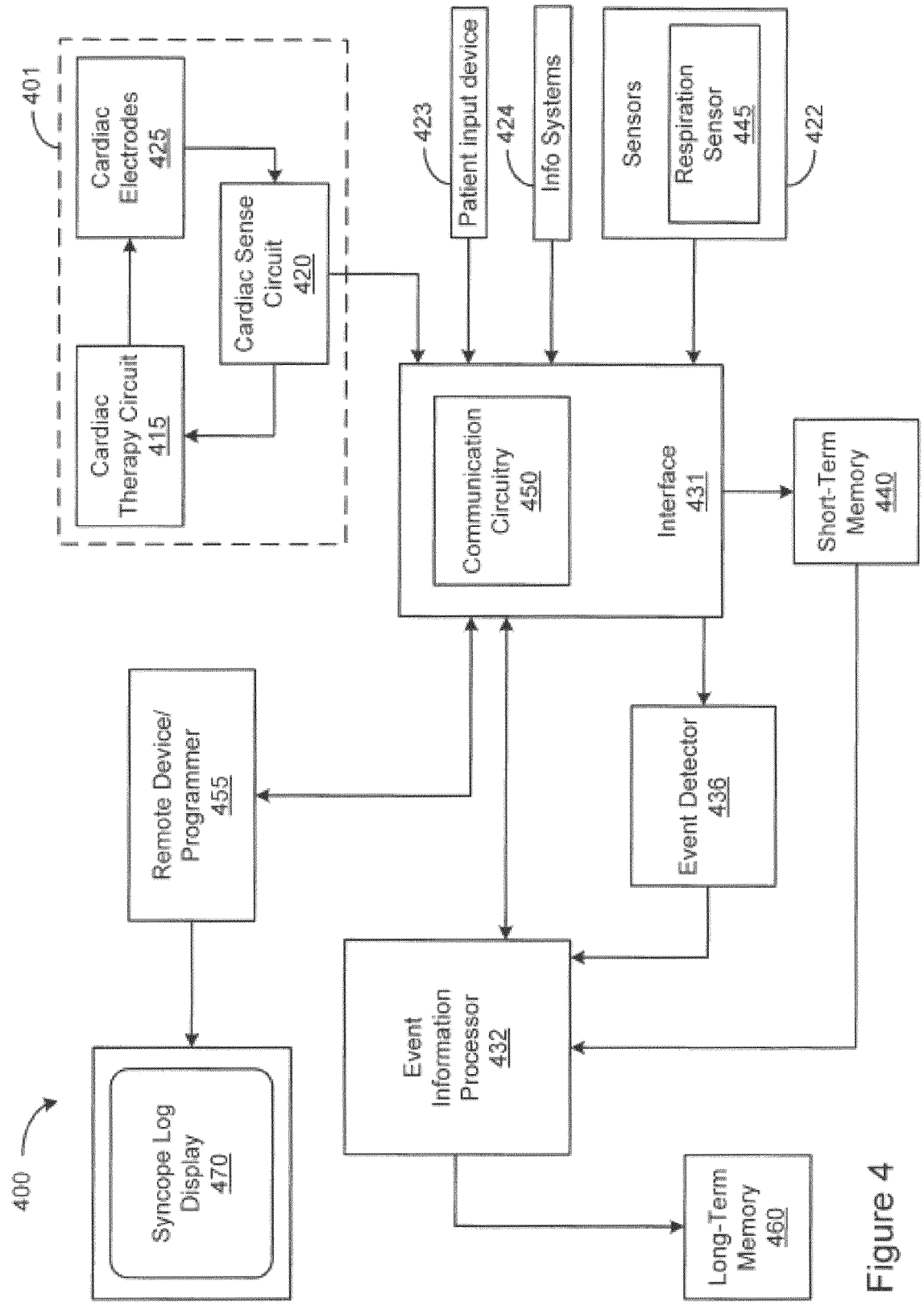
FIG. 4 is a block diagram of a logbook system in accordance with embodiments of the invention.

FIG. 4 is a block diagram of a logbook system 400 in accordance with embodiments of the invention. The syncope logbook system 400 implements an event-driven method of collecting and organizing data related to syncope events.

Various patient conditions may be monitored through sensors 422, patient input devices 423, and/or information systems 424. Data associated with patient conditions may be stored in short term memory 440. One or more of the patient conditions may be used by event detection circuitry 436 to detect or predict the occurrence of a syncope-related event. Detection or prediction of the event initiates the long term storage of information associated with the event by the event information processor 432 into the long term memory 460. For example, the event information processor 432 may collect information supplied by one or more of the sensors 422, patient input devices 423, and information systems 424 before, during, and/or after the detection and/or prediction of the event. The collected information associated with each event is organized as a syncope logbook entry in the syncope logbook. Syncope logbook entries may be stored in long term memory 460, transmitted to a remote device 455, and/or displayed on a display device 470.

Information about various conditions affecting the patient and associated with the syncope-related event may be acquired using sensors 422, patient input devices 423 and/or other information systems 424. The sensors 422 may comprise patient-internal and/or patient-external sensors coupled through leads or wirelessly to the interface 431 of the syncope logbook system 400. The sensors may sense various physiological and/or non-physiological conditions affecting patient respiration, heart functioning or other physiological systems. The patient input device 423 allows the patient to input information relevant to conditions affecting the patient that may be useful in generating a syncope event log. For example, the patient input device 423 may be particularly useful for acquiring information known to the patient, such as information related to patient smoking, drug use, recent exercise level, and/or other patient activities, perceptions and/or symptoms. The information provided by the patient-input device may include patient-known information relevant to the syncope event that is not automatically sensed or detected by the syncope logbook system 400.

The embodiment illustrated in FIG. 4 includes a respiration sensor 445 that senses a physiological condition modulated by patient respiration. In one embodiment, the respiration sensor may comprise a transthoracic impedance sensor. Other methods of sensing respiration are also possible. Such methods may include, for example, the use of patient-external respiratory bands, respiration flowmeter measurements, implantable or patient-external breath sound detection, blood oxygen levels, and/or other processes. The respiration sensor 445 may be used, for example, to acquire a respiration waveform before, during, and/or after a syncope event indicating how the event affects patient respiration. The respiration waveform may be a component of the syncope log entry for the event.

The syncope logbook system 400 may also include one or more information systems 424 such as a remote computing device and/or a network-based server. The event information processor 432 may access the information systems 424 to acquire information from databases and/or other information sources stored on or generated by the remote computing devices and/or servers. The information acquired from the information systems 424 may be recorded in the syncope logbook. In one exemplary implementation, the syncope logbook system 400 may access an internet connected air quality server to collect data related to environmental conditions, such as an ambient pollution index. In another implementation, the syncope logbook system 400 may access the patient's medical history through a patient information server.

The sensors 422, patient input devices 423, and information systems 424 are coupled to other components of the syncope logbook system 400 through interface circuitry 431. The interface 431 may include circuitry for energizing the sensors 422 and/or for detecting and/or processing signals generated by the sensors. The interface 431 may include, for example, driver circuitry, amplifiers, filters, sampling circuitry, and/or A/D converter circuitry for conditioning the signals generated by the sensors.

The interface 431 may also include circuitry 450 for communicating with the patient input device 423, information systems 424, a device programmer 455, an APM system (not shown), or other remote devices. Communication with the patient input device 423, information systems 424 and/or a remote device programmer 455 and/or other remote devices may be implemented using a wired connection or through a wireless communication link, such as a Bluetooth or other wireless link. The communication circuitry 450 may also provide the capability to wirelessly communicate with various sensors, including implantable, subcutaneous, cutaneous, and/or non-implanted sensors.

The syncope logbook system 400 may optionally be implemented as a component of a medical device that includes a therapy system, such as a cardiac rhythm management system 401. The cardiac rhythm management system 401 may include cardiac electrodes 425 electrically coupled to the patient's heart. Cardiac signals sensed by cardiac sense circuitry 420 may be used in the detection and treatment of various anomalies of the heart rhythm. Anomalous heart rhythms may include, for example, a rhythm that is too slow (bradycardia), a heart rhythm that is too fast (tachycardia), and/or a heart rhythm that involves insufficiently synchronized contractions of the atria and/or ventricles, a condition often associated with congestive heart failure.

If an arrhythmia is detected by the cardiac rhythm management system, then a cardiac therapy circuit 415 may deliver cardiac therapy to the heart in the form of electrical stimulation pulses, such as pacing and/or cardioversion/defibrillation pulses. The cardiac signals and/or cardiac conditions, e.g., arrhythmia conditions, derived or detected through the use of the cardiac signals may be factors contributing to syncope-related events. The cardiac information associated with the event may be acquired and organized by the syncope logbook system 400.

Figure 5:
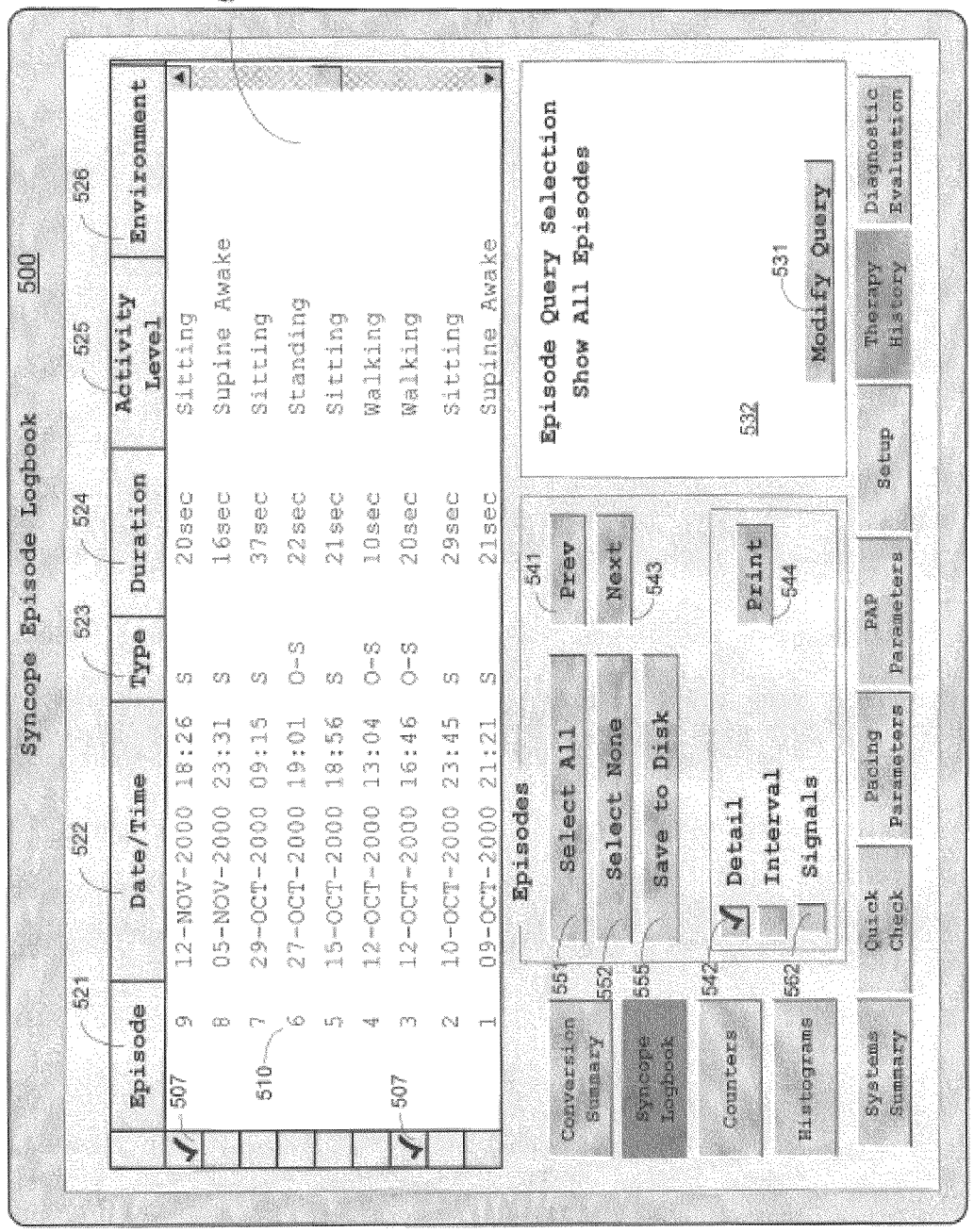
FIG. 5 illustrates an exemplary depiction of a user interface display in accordance with embodiments of the invention.

A user interface may be used to view and/or access the syncope logbook information. FIG. 5 illustrates an exemplary depiction of a user interface display 500. An area 505 of the display may be used to provide textual or graphical information about syncope events. As illustrated in FIG. 5, a menu 510 of syncope events may be presented and may enable the user may access additional information related to the syncope event. The menu 510 may provide a summary of parameters associated with the events contained in the syncope logbook. As illustrated in FIG. 5, one or more summary parameter headings, such as episode number 521, date/time 522, type 523, duration 524, activity level 525, and/or environment 526, among other parameter headings, may be presented at the top of the menu 510 or in another convenient location. The summary parameter headings 521-526 may be programmable, and additional or alternative parameter headings to those depicted in FIG. 5 may be selected, for example. Other or additional types of information may be shown on the display including: heart rate during episode, posture and/or respiration and ECG signals may be displayed. The syncope episode logbook may have the ability to display trends of syncope episodes per day, histograms of number of syncope-related events, heart rate trend and oxygen saturation trend, for example. Other types of information listed in Table 1 above can also be displayed.

The type parameter 523 may contain abbreviations for various syncope events. For example S and O-S may abbreviate standing and opine sitting respectively.

The syncope events displayed as menu items in the menu 510 may be selected by a user according to episode number, date/time, duration, type, number, or by other criteria. The menu items may be selected for display based on various criteria ranges and/or thresholds. For example, in the example screen illustrated in FIG. 5, different groups of events selected as menu items may be selected by activating the modify query button 531. The modify query button 531 and other buttons illustrated on the display may be voice activated, activated through touching the display screen, or by operating a keyboard or pointing device, for example.

In one implementation, activation of the modify query button 531 initiates a dialog session that allows the user to select syncope events to be presented in the menu according various criteria such as by date/time, duration, type, number, or by other criteria ranges or thresholds. In one example, the user may select all syncope-related events to be presented as menu items. In another example, the user may select all events that occurred between a first date and a second date. In yet another example, the user may select all events that occurred while the patient experienced certain environmental conditions, e.g., ambient temperature range and/or humidity range. In yet another example, the user may choose to select all events of the syncope logbook. The selection criteria may be displayed in an episode query selection area 532 of the display. The episode query selection area 532 in the depiction of a syncope logbook display shown in FIG. 5 indicates that all episodes have been selected to be displayed as menu items.

The menu 510 allows the user to choose syncope-related events for which additional textual and/or graphical information is displayed. The additional information provides more detailed information about the selected events beyond the summary information presented in the menu 510. In the exemplary illustration depicted in FIG. 5, the selections are indicated by check marks 507 beside the selected syncope-related events. For convenience, the display may include a select all button 551 and/or a select none button 552. Activation of the select all button 551 causes all events in the menu 510 to be selected. Activation of the select none button 552 causes all events in the menu 510 to be deselected.

Following selection of one or more episodes in the menu, activation of the detail button 542 causes detailed textual information associated with a selected event to be presented on the display screen. The detail information may be displayed in the area of the screen 505 previously occupied by the menu 510, for example. The user may scroll back and forth through the textual information for the one or more selected events using the prey button 541 and the next button 543. The textual information may be printed upon activation of the print button 544, or may be saved to a disk, or other storage medium, through activation of the save to disk button 555.

Graphical information associated with the selected events may be displayed upon activation of the signals button 562. In one implementation, a respiration waveform acquired during, before and/or after a selected event may be displayed in the area 505 of the display previously used for the menu 510. Waveforms of other parameters, e.g., cardiac rhythm, patient activity, may additionally or alternatively be displayed. In one implementation, a marked waveform may be displayed. For example, a marked respiration waveform may include the respiration waveform acquired before, during, and after the event, along with one or more symbols aligned with the respiration waveform to indicate the occurrence of one or more conditions. The symbol may provide a numerical value or a textual description associated with the syncope characteristic, e.g., respiration rate. A user may scroll through the waveforms associated with the selected events using the prey and next buttons 541, 543.

Displaying data stored in a syncope episode logbook can occur automatically or can be initiated by positioning a telemetry wand over the location of the syncope logbook processor. For example, a telemetry wand may be placed over a pulse generator housing a syncope logbook processor. Current information related to syncope episodes stored in the logbook can be transmitted wirelessly to a display device where the organized data can be downloaded and displayed. Additionally, data from a patient disk can be displayed by selecting a read disk function from the utilities menu. Data from other information systems can also be displayed on the syncope episode display. The information related to syncope episodes will be displayed in an organized fashion and the entire list of stored episodes can be viewed by using the scroll bar.

Syncope episode logbooks can be setup in a variety of ways. Particular types of syncope episodes can be stored and others discarded allowing for efficient use of storage space. Logbooks may be switched on during specific periods of the day, for example during a patient's wakeful part of the day.

Storage space can be allocated for particular types of syncope. The data stored for each type can be apportioned based on the physician's desired focus. Additionally, severe syncope episodes can be protected in memory using a prioritized syncope episode protection function.

Figure 6:
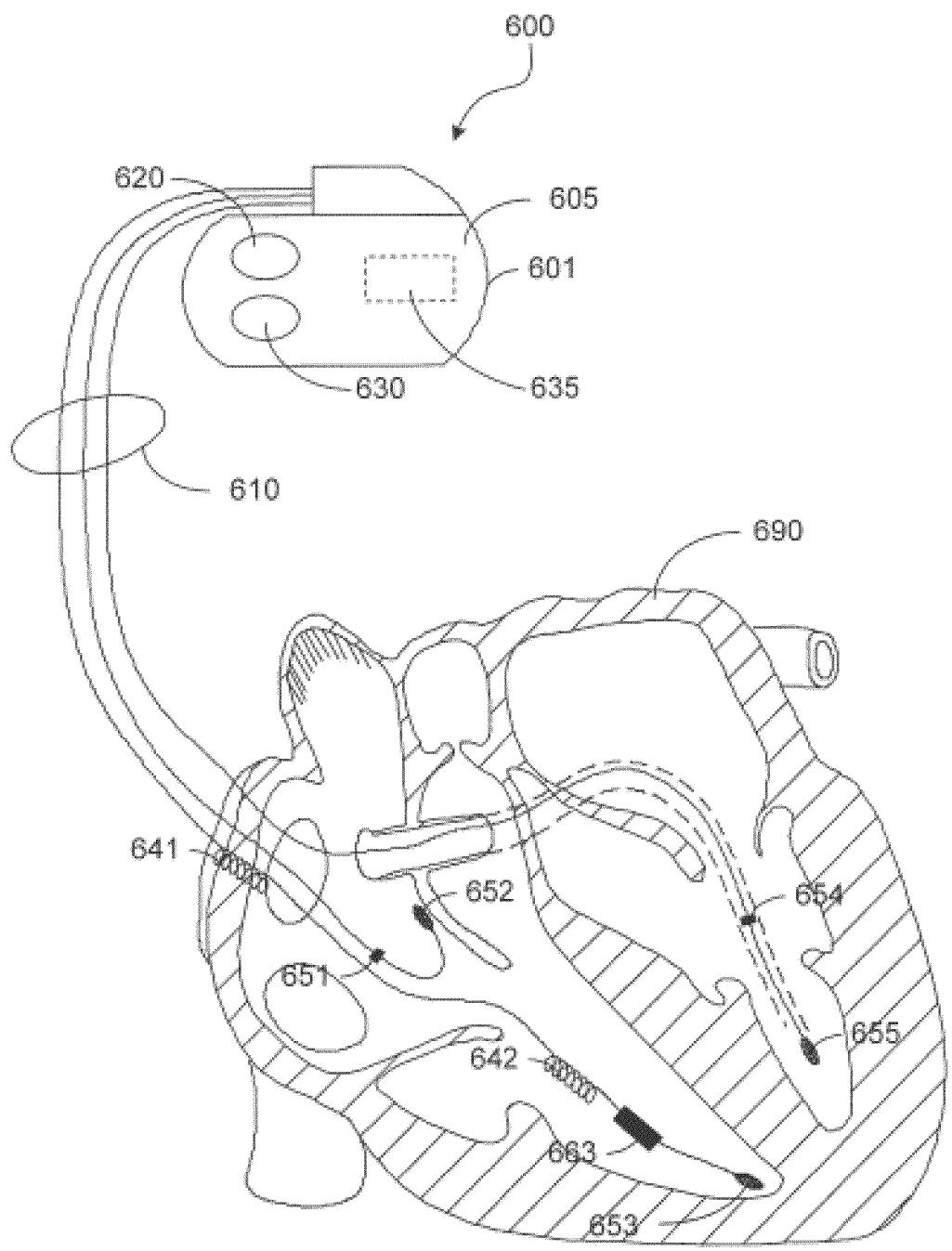
FIG. 6 is a partial view of an implantable device that may include circuitry for implementing a syncope logbook in accordance with embodiments of the invention.

FIG. 6 is a partial view of an implantable device that may include circuitry for implementing a syncope logbook in accordance with embodiments of the invention. In this example, the implantable device comprises a cardiac rhythm management device (CRM) 600 including an implantable pulse generator 605 electrically and physically coupled to an intracardiac lead system 610. The syncope logbook system may alternatively be implemented in a variety of implantable monitoring, diagnostic, and/or therapeutic devices, such as an implantable cardiac monitoring device, an implantable drug delivery device, or an implantable neurostimulation device, for example.

Portions of the intracardiac lead system 610 are inserted into the patient's heart 690. The intracardiac lead system 610 includes one or more electrodes configured to sense electrical cardiac activity of the heart, deliver electrical stimulation to the heart, sense the patient's transthoracic impedance, and/or sense other physiological parameters, e.g., cardiac chamber pressure or temperature. Portions of the housing 601 of the pulse generator 605 may optionally serve as a can electrode.

Communications circuitry is disposed within the housing 601 for facilitating communication between the pulse generator 605 and an external communication device, such as a portable or bed-side communication station, patient-carried/worn communication station, or external programmer, for example. The communications circuitry can also facilitate unidirectional or bidirectional communication with one or more implanted, external, cutaneous, or subcutaneous physiologic or non-physiologic sensors, patient-input devices and/or information systems.

The pulse generator 605 may optionally incorporate a motion detector 620 that may be used to sense various patient conditions including the presence of syncope. A sudden change in movement detected by motion detector 620 may be indicative of syncope, pre-syncope or a fall. For example, motion detector 620 may be implemented as an accelerometer positioned in or on the housing 601 of the pulse generator 605 and may detect a sudden change in patient posture. The motion sensor configured as an accelerometer may also provide respiratory, e.g. rales, coughing, and cardiac, e.g. S1-S4 heart sounds, murmurs, and other acoustic information.

The lead system 610 of the CRM 600 may incorporate one or more transthoracic impedance sensors that may be used to acquire the patient's respiration waveform, or other respiration-related information which may be associated with syncope-related conditions. The transthoracic impedance sensor may include, for example, one or more intracardiac electrodes 641, 642, 651-655, 663 positioned in one or more chambers of the heart 690. The intracardiac electrodes 641, 642, 651-655, 663 may be coupled to impedance drive/sense circuitry 630 positioned within the housing of the pulse generator 605.

In one implementation, impedance drive/sense circuitry 630 generates a current that flows through the tissue between an impedance drive electrode 651 and a can electrode on the housing 601 of the pulse generator 605. The voltage at an impedance sense electrode 652 relative to the can electrode changes as the patient's transthoracic impedance changes. The voltage signal developed between the impedance sense electrode 652 and the can electrode is detected by the impedance sense circuitry 630. Other locations and/or combinations of impedance sense and drive electrodes are also possible.

The voltage signal developed at the impedance sense electrode 652 is proportional to the patient's transthoracic impedance and represents the patient's respiration waveform. The transthoracic impedance increases during respiratory inspiration and decreases during respiratory expiration. The peak-to-peak transition of the transthoracic impedance is proportional to the amount of air moved in one breath, denoted the tidal volume. The amount of air moved per minute is denoted the minute ventilation. A normal "at rest" respiration pattern, e.g., during non-REM sleep, includes regular, rhythmic inspiration expiration cycles without substantial interruptions.

The lead system 610 may include one or more cardiac pace/sense electrodes 651-655 positioned in, on, or about one or more heart chambers for sensing electrical signals from the patient's heart 690 and/or delivering pacing pulses to the heart 590. The intracardiac sense/pace electrodes 651-655, such as those illustrated in FIG. 6, may be used to sense and/or pace one or more chambers of the heart, including the left ventricle, the right ventricle, the left atrium and/or the right atrium. The lead system 610 may include one or more defibrillation electrodes 641, 642 for delivering defibrillation/cardioversion shocks to the heart.

The pulse generator 605 may include circuitry for detecting cardiac arrhythmias and/or for controlling pacing or defibrillation therapy in the form of electrical stimulation pulses or shocks delivered to the heart through the lead system 610. Circuitry for implementing a syncope logbook 635, including interface circuitry, an event detector, an event processor, and/or memory circuitry, as described herein, may be housed within the pulse generator 605. The syncope logbook circuitry may be coupled to various sensors, patient input devices, and/or information systems through leads or through wireless communication links.

Figure 7:
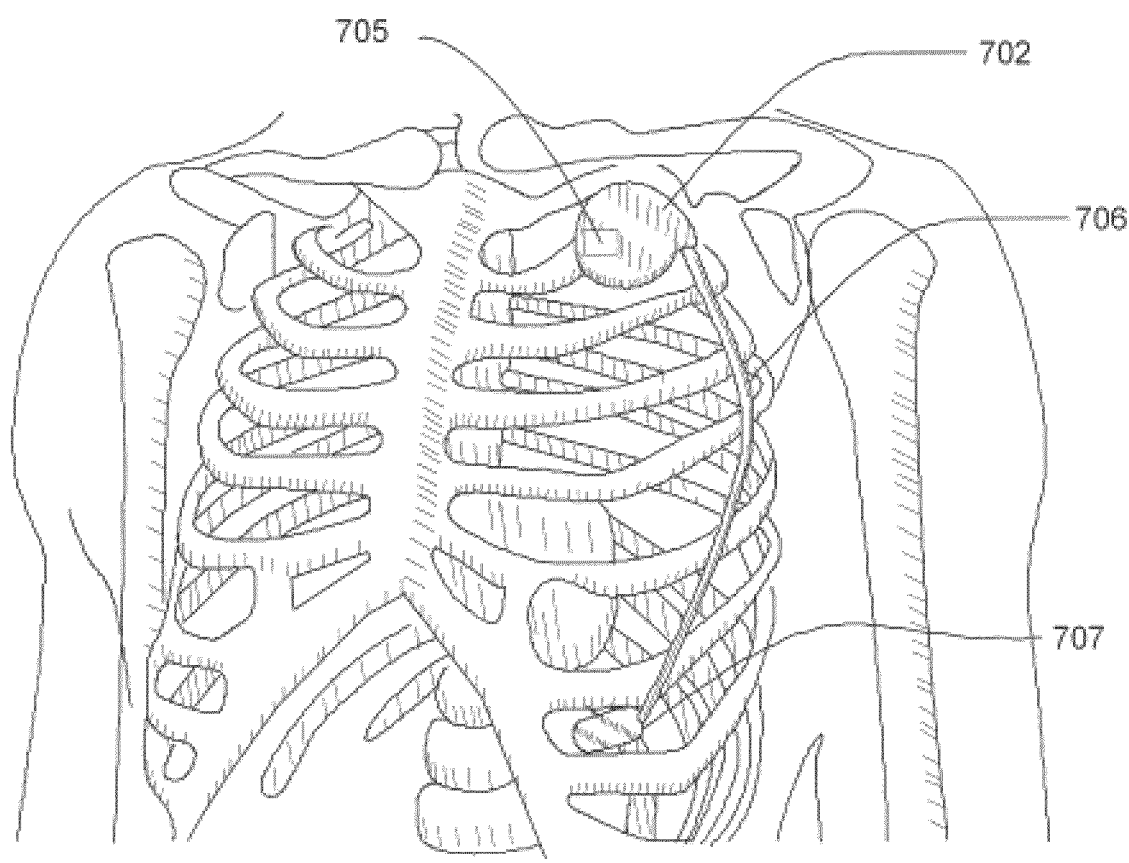
FIG. 7 is a diagram illustrating an implantable transthoracic cardiac device that may be used in connection with acquiring and organizing data for a syncope logbook in accordance with embodiments of the invention.

FIG. 7 is a diagram illustrating an implantable transthoracic cardiac device that may be used in connection with acquiring and organizing data for a syncope logbook in accordance with embodiments of the invention. The implantable device illustrated in FIG. 7 is an implantable transthoracic cardiac sensing and/or stimulation (ITCS) device that may be implanted under the skin in the chest region of a patient. The ITCS device may, for example, be implanted subcutaneously such that all or selected elements of the device are positioned on the patient's front, back, side, or other body locations suitable for sensing cardiac activity and delivering cardiac stimulation therapy. It is understood that elements of the ITCS device may be located at several different body locations, such as in the chest, abdominal, or subclavian region with electrode elements respectively positioned at different regions near, around, in, or on the heart.

Circuitry for implementing a syncope logbook system may be positioned within the primary housing of the ITCS device. The primary housing (e.g., the active or non-active can) of the ITCS device, for example, may be configured for positioning outside of the rib cage at an intercostal or subcostal location, within the abdomen, or in the upper chest region (e.g., subclavian location, such as above the third rib). In one implementation, one or more electrodes may be located on the primary housing and/or at other locations about, but not in direct contact with the heart, great vessel or coronary vasculature.

In another implementation, one or more electrodes may be located in direct contact with the heart, great vessel or coronary vasculature, such as via one or more leads implanted by use of conventional transvenous delivery approaches. In another implementation, for example, one or more subcutaneous electrode subsystems or electrode arrays may be used to sense cardiac activity and deliver cardiac stimulation energy in an ITCS device configuration employing an active can or a configuration employing a non-active can. Electrodes may be situated at anterior and/or posterior locations relative to the heart.

In the configuration shown in FIG. 7, a subcutaneous electrode assembly 707 can be positioned under the skin in the chest region and situated distal from the housing 702. The subcutaneous and, if applicable, housing electrode(s) can be positioned about the heart at various locations and orientations, such as at various anterior and/or posterior locations relative to the heart. The subcutaneous electrode assembly 707 is coupled to circuitry within the housing 702 via a lead assembly 706. One or more conductors (e.g., coils or cables) are provided within the lead assembly 706 and electrically couple the subcutaneous electrode assembly 707 with circuitry in the housing 702. One or more sense, sense/pace or defibrillation electrodes can be situated on the elongated structure of the electrode support, the housing 702, and/or the distal electrode assembly (shown as subcutaneous electrode assembly 707 in the configuration shown in FIG. 7).

It is noted that the electrode and the lead assemblies 707, 706 can be configured to assume a variety of shapes. For example, the lead assembly 706 can have a wedge, chevron, flattened oval, or a ribbon shape, and the subcutaneous electrode assembly 707 can comprise a number of spaced electrodes, such as an array or band of electrodes. Moreover, two or more subcutaneous electrode assemblies 707 can be mounted to multiple electrode support assemblies 706 to achieve a desired spaced relationship amongst subcutaneous electrode assemblies 707.

In particular configurations, the ITCS device may perform functions traditionally performed by cardiac rhythm management devices, such as providing various cardiac monitoring, pacing and/or cardioversion/defibrillation functions. Exemplary pacemaker circuitry, structures and functionality, aspects of which can be incorporated in an ITCS device of a type that may benefit from multi-parameter sensing configurations, are disclosed in commonly owned U.S. Pat. Nos. 4,562,841; 5,284,136; 5,376,476; 5,036,849; 5,540,727; 5,836,987; 6,044,298; and 6,055,454, which are hereby incorporated herein by reference in their respective entireties. It is understood that ITCS device configurations can provide for non-physiologic pacing support in addition to, or to the exclusion of, bradycardia and/or anti-tachycardia pacing therapies. Exemplary cardiac monitoring circuitry, structures and functionality, aspects of which can be incorporated in an ITCS of the present invention, are disclosed in commonly owned U.S. Pat. Nos. 5,313,953; 5,388,578; and 5,411,031, which are hereby incorporated herein by reference in their respective entireties.

An ITCS device can incorporate circuitry, structures and functionality of the subcutaneous implantable medical devices disclosed in commonly owned U.S. Pat. Nos. 5,203, 348; 5,230,337; 5,360,442; 5,366,496; 5,397,342; 5,391,200; 5,545,202; 5,603,732; and 5,916,243 and commonly owned U.S. patent applications "Subcutaneous Cardiac Sensing, Stimulation, Lead Delivery, and Electrode Fixation Systems and Methods," Ser. No. 60/462,272, filed Apr. 11, 2003, and "Hybrid Transthoracic/Intrathoracic Cardiac Stimulation Devices and Methods," published as US 2004/0230229 (Lovett et al.), and "Methods and Systems Involving Subcutaneous Electrode Positioning Relative to A Heart," published as US 2004/0230230 (Lindstrom et al.), which are incorporated by reference.

The housing of the ITCS device may incorporate components of a syncope logbook system 705, including a memory, interface, event processor and/or event detector circuitry. The syncope logbook circuitry may be coupled to one or more sensors, patient input devices, and/or information systems.

In one implementation, the ITCS device may include an impedance sensor configured to sense the patient's transthoracic impedance. The impedance sensor may include the impedance drive/sense circuitry incorporated with the housing 702 of the ITCS device and coupled to impedance electrodes positioned on the can or at other locations of the ITCS device, such as on the subcutaneous electrode assembly 707 and/or lead assembly 706. In one configuration, the impedance drive circuitry generates a current that flows between a subcutaneous impedance drive electrode and a can electrode on the primary housing of the ITCS device. The voltage at a subcutaneous impedance sense electrode relative to the can electrode changes as the patient's transthoracic impedance changes. The voltage signal developed between the impedance sense electrode and the can electrode is sensed by the impedance drive/sense circuitry.

Communications circuitry is disposed within the housing 702 for facilitating communication between the ITCS device and an external communication device, such as a portable or bed-side communication station, patient-carried/worn communication station, or external programmer, for example. The communications circuitry can also facilitate unidirectional or bidirectional communication with one or more external, cutaneous, or subcutaneous physiologic or non-physiologic sensors.

The approaches illustrated and described herein are generally presented in terms of a syncope logbook system configured to organize medical information associated with syncope-related events. The syncope logbook as described in the various embodiments may be utilized in conjunction with other types of medical event logbooks, including, for example, a sleep logbook, medical event logbook, and/or a cardiac arrhythmia logbook. A system may include one or more store information relevant to one or more types of logbooks. Various types of logbooks are described in the commonly owned U.S. Patent Application Publication US 2005/0080348 (Stahmann et al.), U.S. Pat. No. 7,572,225 (Stahmann et al.), and U.S. Pat. Nos. 6,449,504 and 6,843,801, which are incorporated herein by reference.

A number of the examples presented herein involve block diagrams illustrating functional blocks used for in accordance with embodiments of the present invention. It will be understood by those skilled in the art that there exist many possible configurations in which these functional blocks can be arranged and implemented. The examples depicted herein provide examples of possible functional arrangements used to implement the approaches of the invention. The components and functionality depicted as separate or discrete blocks/elements in the figures in general can be implemented in combination with other components and functionality. The depiction of such components and functionality in individual or integral form is for purposes of clarity of explanation, and not of limitation. It is also understood that the components and functionality depicted in the Figures and described herein can be implemented in hardware, software, or a combination of hardware and software.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. An automated method for collecting and organizing information associated with at least one syncope-related event of a patient, the at least one syncope-related event comprising at least a suspected syncope-related event, a verified syncope-related event, or a suspected and verified syncope-related event, the method comprising:
    selecting one or more patient conditions associated with one or more of the syncope-related events for which acquisition of onset data is desired;
    sensing for the one or more selected patient conditions;
    configuring a buffer memory based on buffer memory requirements appropriate for the selected one or more monitored patient conditions;
    temporarily storing information associated with the one or more sensed patient conditions in the configured buffer memory;
    a processor configured for, in response to a triggering event, acquiring occurrence information associated with the one or more sensed patient conditions during occurrence of the one or more of the syncope-related events, the occurrence information temporarily stored in the buffer memory defining onset data associated with occurrence of the one or more of the syncope-related events;
    the processor configuring the buffer memory using buffer memory requirements associated with the triggering event;
    organizing the onset data and the occurrence information as a syncope log entry; and
    storing the syncope log entry;
    wherein at least sensing for the one or more patient conditions, temporarily storing the occurrence information, and organizing the onset data and the occurrence information are respectively performed at least in part implantably.

2. The method of claim 1, wherein configuring the buffer memory is based at least in part on buffer memory size requirements appropriate for the selected one or more monitored patient conditions.

3. The method of claim 1, wherein configuring the buffer memory is based at least in part on sampling rate requirements appropriate for the selected one or more monitored patient conditions.

4. The method of claim 1, wherein configuring the buffer memory is based at least in part on data collection frequency or interval requirements appropriate for the selected one or more monitored patient conditions.

5. The method of claim 1, wherein configuring the buffer memory comprises changing the buffer memory configuration over the course of the one or more of the syncope-related events.

6. The method of claim 1, wherein the one more syncope-related events comprise a plurality of syncope-related event types, and wherein each of a plurality of the triggering events is associated with one of the plurality of syncope-related event types.

7. The method of claim 1, wherein selection of at least one of the patient conditions, triggering event, and buffer memory requirements is based on user input.

8. The method of claim 1, wherein the onset data and the occurrence information comprises cardiovascular system information.

9. The method of claim 1, wherein the onset data and the occurrence information comprises respiratory system information.

10. A medical system for collecting and organizing information associated with at least one syncope-related event of a patient, the at least one syncope-related event comprising a suspected syncope-related event, a verified syncope-related event, or a suspected and verified syncope-related event, the system comprising:
    a sensor arrangement configured to sense for one or more patient conditions;
    a monitoring unit coupled to the sensor arrangement and configured to monitor for one or more sensed patient conditions associated with one or more syncope-related events for which acquisition of onset data is desired;
    a configurable buffer memory and a long-term memory;
    a processor coupled to the buffer memory and configurable by the processor to store information associated with the one or more sensed conditions, the buffer memory configurable by the processor based on buffer memory requirements appropriate for the one or more sensed patient conditions, the processor configured to:
        temporarily store information associated with the one or more sensed patient conditions in the configured buffer memory;
        acquire occurrence information associated with the one or more sensed patient conditions during occurrence of the one or more of the syncope-related events, the occurrence information temporarily stored in the buffer memory defining onset data associated with occurrence of the one or more of the syncope-related events;
        acquire the occurrence information in response to at least one triggering event associated with at least one syncope-related event, the processor configuring the buffer memory using buffer memory requirements associated with the at least one triggering event;
        organize the onset data and the occurrence information as a syncope log entry; and
        store the syncope log entry in the long-term memory;
    wherein at least the sensor arrangement, the monitoring unit, the processor, and the buffer memory comprises an implantable component.

11. The system of claim 10, wherein the processor is configured to acquire the occurrence information in response to a triggering event.

12. The system of claim 10, wherein the processor is configured to acquire the occurrence information in response to one of a plurality of triggering events wherein each of the plurality of the triggering events is associated with one of the plurality of syncope-related events, the processor configuring the buffer memory using buffer memory requirements associated with a particular one of the plurality of triggering events.

13. The system of claim 10, wherein the buffer memory is configurable by the processor based at least in part on buffer memory size requirements appropriate for the selected one or more monitored patient conditions.

14. The system of claim 10, wherein the buffer memory is configurable by the processor based at least in part on sampling rate requirements appropriate for the selected one or more monitored patient conditions.

15. The system of claim 10, wherein the buffer memory is configurable by the processor based at least in part on data collection frequency or interval requirements appropriate for the selected one or more monitored patient conditions.

16. The system of claim 10, wherein the processor is adapted to change the buffer memory configuration over the course of the one or more of the syncope-related events.

17. The system of claim 10, wherein a component of at least one of the sensor arrangement, the monitoring unit, the buffer memory, and the processor is disposed within an implantable cardiac rhythm management device.

18. The system of claim 10, further comprising communications circuitry coupled to the processor, the communications circuitry configured to transmit at least one of the onset data, the occurrence information, and the syncope log entry to a patient-external computing system.

19. The system of claim 10, wherein the sensor arrangement comprises at least one cardiovascular system sensor and at least one respiratory system sensor.

20. The system of claim 10, comprising a user interface coupled to the processor and configured to facilitate user specification of one or more of a syncope-related event to be monitored, a patient condition to be sensed or monitored, and buffer memory requirements.

* * * * *